US012714108B2

(12) United States Patent
Herdy

(10) Patent No.: US 12,714,108 B2
(45) Date of Patent: Aug. 25, 2026

(54) CHEMICAL COMPOSITION AND METHOD FOR MICROBIAL INHIBITING

(71) Applicant: Roger Herdy, Madison, AL (US)

(72) Inventor: Roger Herdy, Madison, AL (US)

( * ) Notice: Subject to any disclaimer, the term of this patent is extended or adjusted under 35 U.S.C. 154(b) by 17 days.

(21) Appl. No.: 18/913,626

(22) Filed: Oct. 11, 2024

(65) Prior Publication Data

US 2025/0120401 A1 Apr. 17, 2025

Related U.S. Application Data

(60) Provisional application No. 63/543,557, filed on Oct. 11, 2023.

(51) Int. Cl.

| | |
|---|---|
| ***A01N 59/00*** | (2006.01) |
| ***A01P 1/00*** | (2006.01) |
| ***A61L 2/23*** | (2006.01) |
| ***A61L 101/24*** | (2006.01) |
| ***C01F 7/02*** | (2022.01) |
| ***E04D 13/00*** | (2006.01) |

(52) U.S. Cl.

CPC ................ *A01N 59/00* (2013.01); *A01P 1/00* (2021.08); *A61L 2/23* (2013.01); *C01F 7/02* (2013.01); *E04D 13/002* (2013.01); *A61L 2101/24* (2020.08); *A61L 2202/15* (2013.01); *A61L 2202/17* (2013.01)

(58) Field of Classification Search

CPC . A01N 59/00; A01N 59/06; A01P 1/00; A01P 3/00; A61L 2/23; A61L 2101/24; A61L 2202/15; A61L 2202/17; C01F 7/02; E04D 13/002

See application file for complete search history.

(56) References Cited

U.S. PATENT DOCUMENTS

2016/0298060 A1* 10/2016 Ludwig ................ C11D 3/3956

FOREIGN PATENT DOCUMENTS

KR 20030096124 A * 12/2003 ............. B01J 20/22

OTHER PUBLICATIONS

Machine translation of KR2003-0096124A (Year: 2003).*

* cited by examiner

*Primary Examiner* — Douglas Lee

(74) *Attorney, Agent, or Firm* — DENNEN IP LAW, LLC

(57) ABSTRACT

The present disclosure is method for treating an asphalt roof using the following steps: (1) clearing debris from the roof; applying fused alpha alumina containing aluminum oxide to cyanobacteria stains; and (3) evenly distribute fused alpha alumina on the cyanobacteria stains such that when it rains, dead cyanobacteria molecules are washed away.

3 Claims, 3 Drawing Sheets

CHEMICAL COMPOSITION AND METHOD FOR MICROBIAL INHIBITING

CROSS REFERENCE TO RELATED APPLICATION

This application claims priority to U.S. Provisional Patent Application Ser. No. 63/543,557 entitled Chemical Composition and Method for Microbial Inhibiting and filed on Oct. 11, 2024, which is incorporated herein by reference.

BACKGROUND

*Gloeocapsa magma* is a species of bacteria in the *Gloeocapsa* genus of cyanobacteria, an ancient line of photosynthesizing bacteria, which photolyze water generating oxygen gas. Ancient cyanobacteria were ancestral to the chloroplasts of all plants on earth. *Gloeocapsa magma* may resemble "algae" in that they are green, but in fact cyanobacteria are bacteria whereas algae are single-celled eukaryotes (cells with nuclei) that are closely related to plants. This is important as most of the patents identified to date that are "competing" with the innovation presented in this patent application are specifically referencing microbes. Microbe organisms fall into two general categories, prokaryotic organisms and eukaryotic organisms. Most prokaryotes are unicellular and classified as bacteria and archaea. Many eukaryotes are multicellular, but some are unicellular such as protozoa, unicellular algae and unicellular fungi.

*Gloeocapsa magma* gained notoriety in the Southeastern United States in the 1990s, but it has since spread throughout most of the rest of the United States and Canada. It is responsible for the black/dark green stains and streaks that form on roofs. These black stains are the bacteria themselves in mass amounts covering the surface of the roof shingles. *Gloeocapsa magma* has been around historically and up through the present, except only in the recent decades has it been considered to have detrimental effects worthy of prevention, due to the switch in the 1980's and 1990's to using crushed limestone in the manufacturing of asphalt roof shingles. This cyanobacterium causes substantial destruction revolving around shingle decay and loss of reflective power. Over time, *Gloeocapsa magma* begins to break down the contents of the shingles by feeding off the limestone granules embedded in the shingles, which decreases the roof's ability to reflect ultra-violet rays of light. Also, the quality of the shingles slowly diminishes. This damage causes shingles to curl up at the corners as well as form raised humps on the surface. This results in broken or disintegrated shingles. Broker or disintegrated shingles increase air conditioning bills and lead to more frequent and very expensive roof repair and reconstruction. The main remediation strategy known to date is frequent (annual) roof cleanings using roof algae cleaners. Often these products contain bleach and other chemicals that are in themselves detrimental to the roof. A preventative approach of installing copper or zinc strips along an upper-level roof boarder also inhibits bacterial growth by killing off new colony formation, however the old stains remain and must be removed manually, which is also detrimental to the life of the roof.

DETAILED DESCRIPTION

The present disclosure describes a strong biocidal ionic solution which will act to kill growth and will be effective even when dispersed over large areas. In one embodiment, the biocidal ionic solution inhibits growth of moss for many years after a single application. The biocidal ionic solution provides a growth-killing product that is inexpensive to procure, apply and/or install as a presence in the asphalt shingles. The biocidal ionic solution of the present disclosure comprises aluminum oxide, which may comprise a multitude of grit and/or micron sized particles.

Metal oxide nanoparticles exhibit optical, electronic, and magnetic properties. The electrostatic interaction of nanoparticles with negatively charged bacterial surfaces draws the particles to the bacteria and promotes their penetration into the membrane. The penetration of nanoparticles into the bacterial cell wall leads to the release of metal ions, which can cause oxidative stress and damage to the bacterial cell membrane. The mechanisms of bacterial killing include the production of reactive oxygen species, cation release, biomolecule damages, adenosine triphosphate (ATP, the organic compound that produces energy to drive and support many processes in living cells) depletion, and membrane interaction.

Broadly, an embodiment of the present invention provides a microbial inhibiting system for asphalt angled roofs. The invention includes dispersing aluminum oxide along the shingles/ridges/slopes of the roofline and are operatively associated with disbursement along or adjacent to a ridge or upper section of the roof. Once installed, potable water or rainwater is directed over the disbursed powder of the invention, causing a reaction therewith, wherein the resulting ionic action from the aluminum oxide (acting as a chemical), will kill growth and allow it to wash away along the roofing membrane, removing any unsightly mold, algae, and moss as the rainwater rolls down the roof during subsequent rainstorms.

Figures 1, 2:
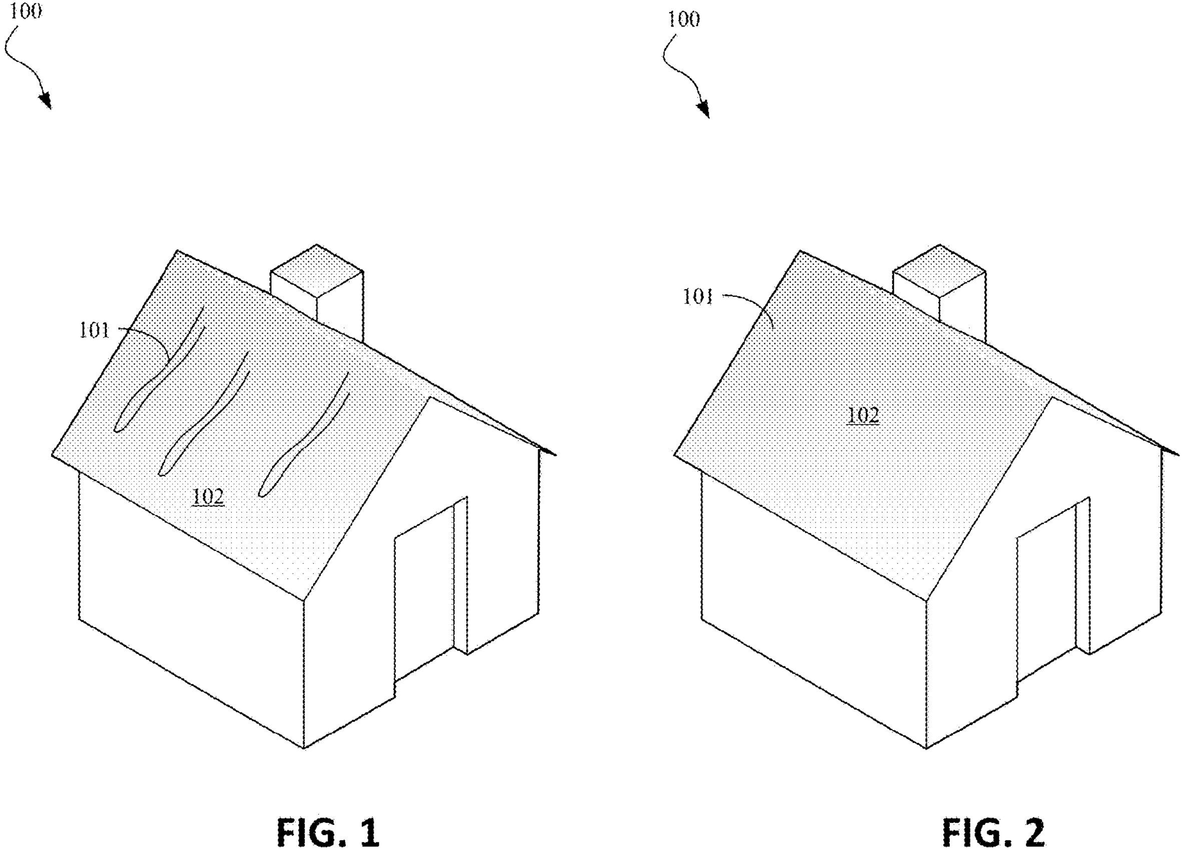
FIG. 1 is a depiction of a house having a roof exhibiting *Gloeocapsa magma.*
FIG. 2 is the house in FIG. 1 after *Gloeocapsa magma* is removed using a chemical composition in accordance with an embodiment of the present disclosure.

FIG. 1 is a house 100 exhibiting black stains 101 on a roof 102 caused by *Gloeocapsa magma* bacteria. As described herein, the *Gloeocapsa magma* bacteria 102 accumulates and shows the black stains as the cyanobacteria develop their dark and hard UV-protective outer. In this regard, the *Gloeocapsa magma* bacteria accumulate over time as it feeds on moisture and the calcium carbonate (limestone) in the roof shingles. This accumulation begins to show the black stains 101 as the cyanobacteria develop their dark and hard UV-protective outer. Note that he *Gloeocapsa magma* have has a simple cellular structure protected by a simple biological sheath of an organic membrane that resembles polymer nanocomposites.

Thus, in one embodiment, the biological sheath can be trapped and mitigated by aluminum oxide. One such aluminum oxide is alumina containing nanoparticles, i.e., small bits of powder.

In one embodiment, the chemical composition of the present disclosure is fused alpha alumina (fused $\alpha$-$Al_2O_3$) and is not to be confused with other alumina groups as it has its own unique, individual and applicable properties. The fused alpha alumina is made in electric arc furnaces by passing a current between vertical carbon electrodes. The heat generated melts the alumina. The furnace consists of a water-cooled steel shell and 3 to 20-ton batches of material are fused at any one time, a way to cheaply produce vast quantities. The fused alumina has a high density, low porosity, low permeability and high refractoriness. As a result of these characteristics, it is used in the manufacture of abrasives and refractories. One of most common use of fused alumina for taking advantage of its abrasive properties is for the process called sandblasting. The chemical composition of the present disclosure uses a finer grit alumina the deeper the "penetration settling" into the granular asphalt roof shingle surface this material would reside.

Fused, alpha alumina interacts with the *Gloeocapsa magma* spores on a molecular level and strips the outer biological sheath of the *Gloeocapsa magma* and surrounds the fused alpha alumina (after a biological process called hydrolysis condensation) with the outer biological sheath to form a carbon shell.

This both kills the *Gloeocapsa magma* spores and offers a very convenient and nicely detached particle to both be washed away by rainwater and to scrub (along with some of the available nanoparticle sandblasting material of alpha alumina), the other dead *Gloeocapsa magma* spore stains from the roof. This is what over time the roof gets cleaner and cleaner: rainwater is scrubbing the roof without human interaction and in a gentle yet effective manner. Interact, compromise, then wash away.

FIG. 2 is house 100 exhibiting roof 102 after the microbial inhibiting chemical composition is applied to the roof 102.

Figure 3:
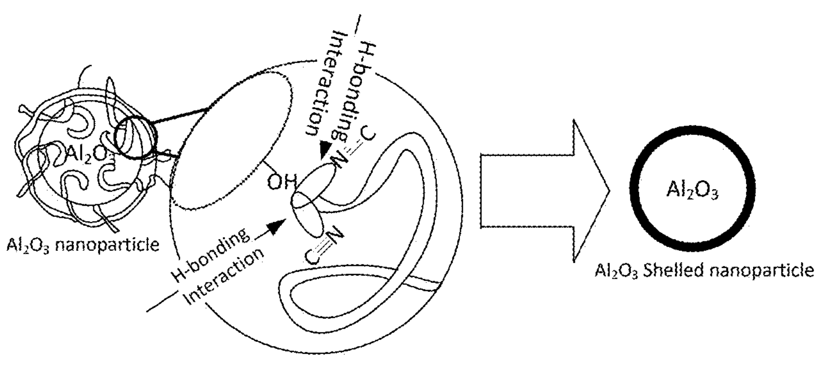
FIG. 3 is a diagram illustrating a process of stripping *Gloeocapsa magma* and surrounding and forming a carbon shell.

FIG. 3 is a diagram illustrating the process of getting rid of the black stains 102 (FIG. 1) from the roof 101 (FIG. 1). The alumina nanoparticles are from an amphoteric oxide and occur in nature as a mineral corundum ($Al_2O_3$); diaspore ($Al_2O_3$—$H_2O$); gibbsite ($Al_2O_3$ $3H_2O$); and most commonly as bauxite, an impure form of hexagonal gibbsite. The known group of alumina is low-temperature alumina $Al_2O_3$ n $H_2O$ (0-n-6). This group obtained via dehydration of boehmite and bayerite at ~600° C., (as $\eta$, $\chi$, $\rho$, and $\gamma$-$Al_2O_3$). Meanwhile, high-temperature alumina (anhydrous $Al_2O_3$, as $\theta$, $\delta$, $\kappa$ and $\alpha$-$Al_2O_3$) is obtained at temperatures ranging from ~900 to 1000° C.

The chemical composition of the present disclosure is fused alpha alumina (fused $\alpha$-$Al_2O_3$). Fused alpha alumina is made in electric arc furnaces by passing a current between vertical carbon electrodes. The heat generated melts the alumina. The furnace consists of a water-cooled steel shell and 3 to 20-ton batches of material fused at any one time, a way to cheaply produce vast quantities. The fused alumina has a high density, low porosity, low permeability and high refractoriness. As a result of these characteristics, it is used in the manufacture of abrasives and refractories. One of most common use of fused alumina for taking advantage of its abrasive properties is for the process called sandblasting. The alpha alumina has a very fine grit composition, thus the deeper the "penetration settling" into the granular asphalt roof shingle surface this material would reside.

Figure 4:
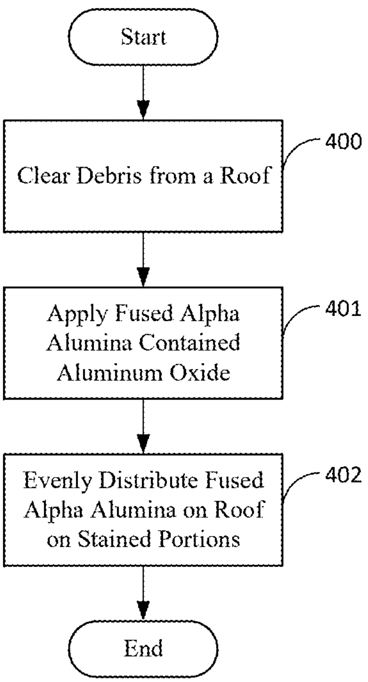
FIG. 4 is a flowchart of a method in accordance with an embodiment of the present disclosure.

FIG. 4 is a flowchart of a method in accordance with an embodiment of the present disclosure.

In step 400, the debris is removed from roof 101 (FIG. 1). For example, leaves and/or branches are removed from the roof 101.

In step 401, alpha alumina containing aluminum oxide is applied to the roof 101. Specifically, the fused alpha alumina is applied to the stains 102. Application of the alpha alumina may be done using a shaking process. Alpha alumina is a powder, as described above.

In step 402, the alpha alumina is evenly distributed across the roof. In one embodiment, even distribution may be accomplished by spraying water on the applied alpha alumina to disperse it into the asphalt shingles.

Thereafter, dead spores are washed away by the scrubbing action of the alpha alumina. This is accomplished each time rain falls on the roof 101.

What I claim is:

1. A method for treating an asphalt roof, comprising:
clearing debris from the roof;
apply fused alpha alumina containing aluminum oxide to cyanobacteria stains; and
evenly distribute the fused alpha alumina on the cyanobacteria stains such that when it rains, dead cyanobacteria molecules are washed away.

2. The method of claim 1, wherein the application comprises using a shaker for shaking the alpha alumina onto the roof.

3. The method of claim 1, wherein the distribution step further comprises spraying the alpha alumina so that the alpha alumina is embedded in the asphalt shingles.

* * * * *